(12) United States Patent
Goto et al.

(10) Patent No.: US 9,163,161 B2
(45) Date of Patent: Oct. 20, 2015

(54) POLYURETHANE AQUEOUS DISPERSION, FORMED FILM OBTAINED FROM SAME, AND GLOVE

(71) Applicants: TOYO POLYMER CO., LTD., Osaka-shi, Osaka (JP); SHOWA GLOVE Co., Himeji-shi, Hyogo (JP)

(72) Inventors: Michiro Goto, Ibaraki (JP); Kenji Shimizu, Ibaraki (JP); Yoshio Seki, Ibaraki (JP); Tomoya Genmoto, Ibaraki (JP); Chie Ipponsugi, Ibaraki (JP); Naohito Higuchi, Himeji (JP)

(73) Assignee: TOYO POLYMER CO., LTD., Osaka (JP)

(*) Notice: Subject to any disclaimer, the term of this patent is extended or adjusted under 35 U.S.C. 154(b) by 120 days.

(21) Appl. No.: 14/347,828

(22) PCT Filed: May 24, 2013

(86) PCT No.: PCT/JP2013/064491
§ 371 (c)(1),
(2) Date: Mar. 27, 2014

(87) PCT Pub. No.: WO2013/176257
PCT Pub. Date: Nov. 28, 2013

(65) Prior Publication Data
US 2014/0235786 A1    Aug. 21, 2014

(30) Foreign Application Priority Data

May 25, 2012  (JP) ................................ 2012-120250

(51) Int. Cl.
| | | |
|---|---|---|
| A41D 19/00 | (2006.01) | |
| B29C 47/00 | (2006.01) | |
| B29D 22/00 | (2006.01) | |
| B29D 23/00 | (2006.01) | |
| B32B 1/06 | (2006.01) | |
| C08G 18/00 | (2006.01) | |
| C08G 18/08 | (2006.01) | |
| C08G 18/10 | (2006.01) | |
| C08G 18/28 | (2006.01) | |
| C08G 18/30 | (2006.01) | |
| C08G 18/32 | (2006.01) | |
| C08G 18/60 | (2006.01) | |
| C08G 18/70 | (2006.01) | |
| C08G 18/71 | (2006.01) | |

(Continued)

(52) U.S. Cl.
CPC .......... *C09D 175/08* (2013.01); *A41D 19/0055* (2013.01); *A61B 19/04* (2013.01); *C08G 18/0823* (2013.01); *C08G 18/0866* (2013.01); *C08G 18/12* (2013.01); *C08G 18/3206* (2013.01); *C08G 18/3234* (2013.01); *C08G 18/348* (2013.01); *C08G 18/4018* (2013.01); *C08G 18/44* (2013.01); *C08G 18/4837* (2013.01); *C08G 18/4854* (2013.01); *C08G 18/721* (2013.01); *C08G 18/755* (2013.01); *C08G 18/758* (2013.01); *C08G 18/7671* (2013.01); *C08J 5/02* (2013.01); *C08J 5/18* (2013.01); *C08J 2375/08* (2013.01)

(58) Field of Classification Search
CPC ............... A41D 19/0055; A61B 19/04; C08G 18/4837; C08G 18/4854; C08G 18/721; C08G 18/12; C08G 18/4018; C08G 18/44; C08G 18/755; C08G 18/758; C08G 18/7671; C08G 18/0823; C08G 18/0866; C08G 18/3234; C08G 18/348; C08G 18/3206; C08J 5/02; C08J 5/18; C08J 2375/08; C09D 175/08
USPC ............ 524/589, 590, 591, 839, 840; 528/44, 528/60, 65, 66, 67, 68, 76, 80, 85; 2/168; 428/36.9
See application file for complete search history.

(56) References Cited

U.S. PATENT DOCUMENTS

| 5,461,122 A * | 10/1995 | Yilgor et al. | ................ 525/474 |
| 7,771,806 B2 * | 8/2010 | Kim et al. | .................. 428/36.9 |

FOREIGN PATENT DOCUMENTS

| JP | 62-260811 A | 11/1987 |
| JP | 03-203920 A | 9/1991 |

(Continued)

OTHER PUBLICATIONS

International Search Report mailed Aug. 20, 2013, in International Application No. PCT/JP2013/064491, filed May 24, 2013.

*Primary Examiner* — Patrick Niland
(74) *Attorney, Agent, or Firm* — Hauptman Ham, LLP

(57) ABSTRACT

Provided is a polyurethane aqueous dispersion characterized in having practical utility in terms of processing suitability when a formed film is produced by salt coagulation method, and characterized in that a formed film obtained from the same has practical utility in terms of resistance against ethanol water. A polyurethane aqueous dispersion for a formed film, the formed film being obtained by using the polyurethane aqueous dispersion and a coagulant liquid in combination, is obtained by: neutralizing an isocyanate group-terminated prepolymer obtained by reaction of a polyisocyanate (A) composed of diphenylmethane diisocyanate and alicyclic diisocyanate, a random copolymer (B) of ethylene oxide and tetrahydrofuran, a polyol (C) having a number average molecular weight of 1000 to 5000, a polyhydric alcohol-based chain extender (D) having a number average molecular weight of 400 or less, and a diol compound (E) having a carboxyl group; and dispersing the obtained neutralized substance in water, and thereafter causing a chain extension reaction using an amine-based chain extender (F).

10 Claims, No Drawings

(51) Int. Cl.
*C08L 75/00* (2006.01)
*C09D 175/08* (2006.01)
*A61B 19/04* (2006.01)
*C08G 18/34* (2006.01)
*C08J 5/02* (2006.01)
*C08G 18/48* (2006.01)
*C08G 18/72* (2006.01)
*C08J 5/18* (2006.01)
*C08G 18/12* (2006.01)
*C08G 18/40* (2006.01)
*C08G 18/44* (2006.01)
*C08G 18/75* (2006.01)
*C08G 18/76* (2006.01)

(56) References Cited

FOREIGN PATENT DOCUMENTS

| | | |
|---|---|---|
| JP | 2010-053159 A | 3/2010 |
| JP | 2011-137052 A | 7/2011 |
| JP | 2011-213867 A | 10/2011 |
| JP | 2011-213884 A | 10/2011 |

\* cited by examiner

POLYURETHANE AQUEOUS DISPERSION, FORMED FILM OBTAINED FROM SAME, AND GLOVE

RELATED APPLICATIONS

The present application is a National Phase of International Application Number PCT/JP2013/064491, filed May 24, 2013, and claims priority from Japanese Application Number 2012-120250, filed May 25, 2012.

TECHNICAL FIELD

The present invention relates to a polyurethane aqueous dispersion, a formed film obtained from the same, and a glove.

BACKGROUND ART

A polyurethane aqueous dispersion is used in, for example, paints, adhesives, synthetic leather, artificial leather, formed films and the like. Among these, examples of the formed films include gloves, finger stalls, condoms and the like, which are typically produced by salt coagulation method (Patent Document 1). In the configuration of Patent Document 1, in order to obtain a formed film having a uniform film thickness, a polyurethane aqueous dispersion having specific viscometric properties is used. With regard to a formed film, however, demand characteristics other than the above-described properties, for example, durability in the case where it is exposed to ethanol water repeatedly, stuffiness resistance in the case where the formed film is worn for a long time, and the like are required in some cases, but the document 1 discloses almost nothing other than the film thickness uniformity.

PRIOR ART DOCUMENT

Patent Document

Patent Document 1 JP2011-137052A

SUMMARY OF THE INVENTION

Problem to be Solved by the Invention

The present invention was made in light of the above-described circumstances, and the main purpose of the same is to provide a polyurethane aqueous dispersion characterized in having practical utility in terms of processing suitability when a formed film is produced from the same by salt coagulation method, and characterized in that a formed film obtained from the same has practical utility in terms of resistance against ethanol water.

Means for Solving the Problem

The inventors of the present invention earnestly studied to solve the above-described problem. As a result, they found that, among various polyols, a polyurethane aqueous dispersion formed with a random copolymer of ethylene oxide and tetrahydrofuran as a raw material has practical utility in terms of processing suitability when a formed film is produced from the same by salt coagulation method, and a formed film obtained from the polyurethane aqueous dispersion has practical utility in terms of resistance against ethanol water. Thus, the inventors completed the present invention.

The present invention is as follows.

[1] A polyurethane aqueous dispersion for a formed film, the formed film being obtained by using the polyurethane aqueous dispersion and a coagulant liquid in combination, the polyurethane aqueous dispersion being obtained by: neutralizing an isocyanate group-terminated prepolymer obtained by reaction of a polyisocyanate (A) composed of diphenylmethane diisocyanate (a1) and alicyclic diisocyanate (a2), a random copolymer (B) of ethylene oxide and tetrahydrofuran, a polyol (C) having a number average molecular weight of 1000 to 5000, a polyhydric alcohol-based chain extender (D) having a number average molecular weight of 400 or less, and a diol compound (E) having a carboxyl group; and dispersing the obtained neutralized substance in water, and thereafter causing a chain extension reaction using an amine-based chain extender (F).

[2] The polyurethane aqueous dispersion according to [1], wherein a molar ratio between the component (a1) and the component (a2), which is (a1)/(a2), is in a range of 20/80 to 80/20.

[3] The polyurethane aqueous dispersion according to [2], wherein the component (a2) is at least one selected from the group consisting of hydrogenated diphenylmethane diisocyanate and isophorone diisocyanate.

[4] The polyurethane aqueous dispersion according to any one of [1] to [3], wherein the component (B) has a number average molecular weight of 800 to 4000, and a molar ratio between units of the ethylene oxide (EO) and units of tetrahydrofuran (THF), which is EO/THF, is in a range of 80/20 to 10/90.

[5] The polyurethane aqueous dispersion according to [4], wherein a content of EO is 2.8% by weight or more with respect to polyurethane in the polyurethane aqueous dispersion.

[6] The polyurethane aqueous dispersion according to [5], wherein the content of EO is 2.8% by weight to 14% by weight.

[7] The polyurethane aqueous dispersion according to [4], wherein a content of 2,4'-diphenylmethane diisocyanate (2,4'-MDI) in the component (a1) is 40% by weight or more.

[8] The polyurethane aqueous dispersion according to [7], wherein the content of 2,4'-MDI is 70% by weight or more.

[9] A formed film obtained by using the polyurethane aqueous dispersion according to any one of [1] to [8] and a coagulant liquid in combination.

[10] A glove obtained by using the polyurethane aqueous dispersion according to any one of [1] to [8] and a coagulant liquid in combination.

Effect of the Invention

The polyurethane aqueous dispersion of the present invention has practical utility in terms of processing suitability when a formed film is produced from the same by salt coagulation method, and a formed film obtained from the same has practical utility in terms of resistance against ethanol water. Further, by adjusting the content of ethylene oxide units with respect to polyurethane in the polyurethane aqueous dispersion, the obtained formed film has practical utility in terms of moisture permeability, in addition to the above-described effect.

DESCRIPTION OF PREFERRED EMBODIMENTS

The polyurethane aqueous dispersion of the present invention is obtained by the following steps: neutralizing an isocyanate group-terminated prepolymer obtained by causing reaction of a polyisocyanate (A) composed of diphenylmethane diisocyanate (MDI) and alicyclic diisocyanate, a random copolymer (B) of ethylene oxide and tetrahydrofuran, a polyol (C) having a number average molecular weight of 1000 to 5000, a polyhydric alcohol-based chain extender (D) having a number average molecular weight of 400 or less, a diol compound (E) having a carboxyl group, and another component as required; emulsifying and dispersing the obtained neutralized substance in water; and thereafter, causing chain extension reaction using an amine-based chain extender (F).

The present invention is characterized in that MDI (hereinafter referred to by abbreviation as "the component (a1)" in some cases) and the alicyclic diisocyanate (hereinafter referred to by abbreviation as "the component (a2)" in some cases) are used in combination, as the polyisocyanate (A) (hereinafter simply referred to by abbreviation as "the component (A)" in some cases). In the case where the component (a1) is used alone, a polyurethane aqueous dispersion cannot be produced, and in the case where the component (a2) is used alone, a formed film produced from a polyurethane aqueous dispersion by salt coagulation method has a poorer resistance against ethanol water. By using the component (a1) and the component (a2) in combination, practical utility can be achieved in terms of processing suitability in the case where a formed film is produced by salt coagulation method, and the formed film obtained has practical utility in terms of resistance against ethanol water.

In the present invention, "the processing suitability in the case where a formed film is produced by salt coagulation method" is evaluated as follows. A ceramic plate is immersed in a 10% calcium nitrate aqueous solution, picked up out of the solution, and then, dried by heating. Subsequently the ceramic plate is immersed in the polyurethane aqueous dispersion of the present invention, and picked up out of the dispersion. A gel coating (film thickness: about 100 μm) formed on the ceramic plate is peeled out of the ceramic plate. Subsequently, a gelation strength when the gel coating thus peeled is stretched by fingers is measured, which is used in the evaluation. The evaluation criteria are as follows: in the case where a coating is formed and the coating becomes elongated, the polyurethane aqueous dispersion is determined to have practical utility, and in the case where a coating is formed and the coating has rubber elasticity (stretchability), the polyurethane aqueous dispersion is determined to have excellent practical utility. The processing suitability in the case where a formed film is produced by salt coagulation method is regarded as an index that is used, when a formed film is produced by salt coagulation method, for preventing uneven thickness and rip from occurring so as to obtain a product having a uniform film thickness.

In the present invention, "the resistance against ethanol water of the formed film" is evaluated as follows. From a film (film thickness: about 100 μm) produced by salt coagulation method, a test specimen is cut out using a JIS No. 3 dumbbell, immersed in a 70% ethyl alcohol aqueous solution (23° C.±2° C.) for 30 minutes, and taken out. This test specimen is subjected to a tensile strength test, and the resistance against ethanol water is evaluated according to the determined tensile strength. The evaluation criteria are as follows: when the tensile strength is 4 MPa or more and less than 10 MPa, the formed film is determined to have practical utility, and when the tensile strength is 10 MPa or more, the formed film is determined to have excellent practical utility. The resistance against ethanol water of the formed film is regarded as an index for determining durability of the formed film.

Examples of MDI include 2,2'-diphenylmethane diisocyanate (2,2'-MDI), 2,4'-diphenylmethane diisocyanate (2,4'-MDI), and 4,4'-diphenylmethane diisocyanate (4,4'-MDI). One of the above-described compounds can be used alone, or alternatively, two or more of the same can be used in combination.

The alicyclic diisocyanate is not limited particularly, and examples of the same include isophorone diisocyanate 4,4'-dicyclohexylmethane diisocyanate (hydrogenated MDI), 1,4-bis(isocyanatomethyl)cyclohexane, 1,3-bis(isocyanatomethyl)cyclohexane, methyl cyclohexylene diisocyanate (hydrogenated TDI), bis(2-isocyanatoethyl)-4-cyclohexene-1,2-dicarboxylate, and 2,5- or 2,6-norbornane diisocyanate. One of the above-described compounds can be used alone, or alternatively, two or more of the same can be used in combination.

The combination of MDI and alicyclic diisocyanate is not limited particularly, but the combination of MDI and IPDI, and the combination of MDI and hydrogenated MDI are preferred in particular, from the viewpoint that such a combination provides practical utility in terms of processing suitability in the case where a formed film is produced by salt coagulation method, and from the viewpoint that a formed film obtained has practical utility in terms of resistance against ethanol water.

In the present invention, the content ratio between the component (a1) and the component (a2) is not limited particularly, but the ratio (a1)/(a2) is preferably in a range of 20/80 to 80/20 (molar ratio), from the viewpoint that such a ratio provides practical utility in terms of processing suitability in the case where a formed film is produced by salt coagulation method, and from the viewpoint that a formed film obtained has practical utility in terms of resistance against ethanol water.

In the polyurethane aqueous dispersion of the present invention, a polyisocyanate other than the above-mentioned components (a1) and (a2), as the component (A), can be used in addition as required, on the premise that practical utility can be achieved in terms of processing suitability when formed film is produced by salt coagulation method, as well as in terms resistance against ethanol water of a formed film obtained. Examples of the polyisocyanate that can be used in addition include aromatic diisocyanates such as 2,4-trilene diisocyanate, 2,6-trilene diisocyanate, xylene-1,4-diisocyanate, xylene-1,3-diisocyanate, tetramethyl xylene diisocyanate, m-phenylene diisocyanate, and p-phenylene diisocyanate; and aliphatic diisocyanates such as tetramethylene diisocyanate, hexamethylene diisocyanate, pentane-1,5-diisocyanate, 3-methyl-1,5-pentane diisocyanate, and lysine diisocyanate. Further, the examples also include polymeric products of those described above, products obtained by reaction of those described above with active hydrogen group-containing compounds, such as urethane compounds, urea compounds, allophanate compounds, biuret compounds, carbodiimide compounds, uretonimine compounds, uretdione compounds, and isocyanurate compounds. Still further, the examples also include mixtures including two or more among the above-described series of isocyanate group-containing compounds.

The present invention is characterized in that as a polyol, the random copolymer (B) (hereinafter referred to by abbreviation as "the component (B)" in some cases) of ethylene oxide and tetrahydrofuran, and the polyol (C) (hereinafter referred to by abbreviation as "the component (C)" in some cases) having a number average molecular weight of 1000 to 5000 are used in combination. By using the component (B) and the component (C) in combination as the polyol, practical utility can be achieved in terms of processing suitability when a formed film is produced by salt coagulation method, as well as in terms of the resistance against ethanol water of a formed film obtained.

The component (B) is one type of a polyether polyol, and the molar ratio (EO/THF) between the ethylene oxide unit (EO) and the tetrahydrofuran unit (THF) is preferably in a range of 80/20 to 10/90, and more preferably in a range of 70/30 to 20/80. One type of the component (B) can be used alone, or alternatively, two or more types of the components (B) can be used in combination. The component (B) preferably has a number average molecular weight of 800 to 4000, and more preferably 900 to 3500.

The component (C) is not limited particularly as long as it has a number average molecular weight of 1000 to 5000 and the above-described effects can be achieved when the component (C) is used in combination with the component (B), and examples of the same include polycarbonate polyols, polyester polyols, and polyether polyols other than the component (B). One type of the same can be used alone, or alternatively, two or more types of the same can be used in combination.

Examples of the polycarbonate polyol include those obtained by dealcoholization reaction, dephenolization reaction, or the like between one type or two or more types of polyols selected from those shown below and one type or two or more types of carbonates selected from those shown below. Examples of the polyol include ethylene glycol, 1,2-propanediol, 1,3-propanediol, 1,2-butanediol, 1,3-butanediol, 1,4-butanediol, 1,5-pentanediol, 1,6-hexanediol, 3-methyl-1,5-pentanediol, neopentyl glycol, 1,8-octanediol, 1,9-nonanediol, diethylene glycol, dipropylene glycol, 1,4-cyclohexane dimethanol, ethylene oxide- or propylene oxide-adducts of bisphenol A, trimethylol propane, glycerin, and pentaerythritol. Examples of the carbonate include diethylene carbonate, dimethyl carbonate, diethyl carbonate, and diphenyl carbonate. One type of the above-described polycarbonate polyol can be used alone, or alternatively, two or more types of the same can be used in combination.

Examples of the polyester polyol include those obtained by polycondensation reaction of one type or two or more types of diprotic acids selected from those shown below and one type or two or more types of the polyols used in the synthesis of the above-described polycarbonate polyols. Examples of the diprotic acid include phthalic acid, isophthalic acid, terephthalic acid, naphthalene dicarboxylic acid, succinic acid, malonic acid, adipic acid, sebacic acid, 1,4-cyclohexyl dicarboxylic acid, maleic acid, and fumaric acid. One type of the above-described polyester polyol can be used alone, or alternatively, two or more types of the same can be used in combination.

Examples of the polyether polyol include reaction products obtained by addition polymerization of one type or two or more types of monomers shown below, in which one type or two or more types of compounds having at least two active hydrogen atoms each and working as an initiator. Examples of the aforementioned monomer include ethylene oxide, propylene oxide, butylene oxide, styrene oxide, epichlorohydrin, and cyclohexylene. Examples of the initiator include ethylene glycol, propylene glycol, 1,3-butylene glycol, 1,4-butanediol, 1,6-hexanediol, diethylene glycol, neopentyl glycol, catechol, hydroquinone, and bisphenol A. In the case of the reaction product obtained by addition polymerization of two or more types of monomers, the reaction product may be a block addition product, a random addition product, or alternatively, a mixture system of the two. More specifically, examples of the polyether polyol include polyethylene glycol, polypropylene glycol, and polytetramethylene glycol. One type of the above-described polyether polyol can be used alone, or alternatively, two or more types of the same can be used in combination.

Examples of the polyhydric alcohol-based chain extender (D) having a number average molecular weight of 400 or less (hereinafter referred to by abbreviation as "the component (D)" in some cases) include: linear aliphatic glycols such as ethylene glycol, propylene glycol, 1,3-propanediol, 1,3-butanediol, 1,4-butanediol, 1,5-pentanediol, 3-methyl-1,5-pentanediol, 1,6-hexanediol, diethylene glycol, triethylene glycol, tetraethylene glycol, dipropylene glycol, tripropylene glycol, polyethylene glycol, 1,8-octanediol, and 1,9-nonanediol; aliphatic branched glycols such as neopentyl glycol, 3-methyl-1,5-pentanediol, 2-methyl-1,3-propanediol, 2-butyl-2-ethyl-1,3-propanediol, and 2-methyl-1,8-octanediol; alicyclic glycols such as 1,4-cyclohexane diol, 1,4-cyclohexane dimethanol, and hydrogenated bisphenol A; and multifunctional glycols such as glycerin, trimethylol propane, tributylol propane, pentaerythritol, and sorbitol. One type of the component (D) can be used alone, or alternatively, two or more types of the same can be used in combination.

As the diol compound (E) having a carboxyl group (hereinafter referred to by abbreviation as "the component (E)" in some cases), a dialkylol alkanoic acid having 6 to 24 carbon atoms can be used. Examples of the same include 2,2-dimethylol propionic acid (DMPA), 2,2-dimethylol butanoic acid (DMBA), 2,2-dimethylol heptanoic acid, and 2,2-dimethylol octanoic acid. Salts of these, for example, salts of amines (triethylamine, alkanolamine, morpholine, and the like) and/or salts of alkaline metals (sodium salts and the like) can be used as well. One type of the above-described compound can be used alone, or alternatively, two or more type of the same can be used in combination.

Examples of the amine-based chain extender (F) (hereinafter referred to by abbreviation as "the component (F)" in some cases) include ethylenediamine, propylenediamine, hexamethylenediamine, 4,4'-diaminodicyclohexylmethane, piperadine, 2-methyl piperadine, isophoronediamine, diethylenetriamine, triethylenetetramine, and hydrazine. One type of the above-described compound can be used alone, or alternatively, two or more types of the same can be used in combination.

Regarding other components, the following components can be added for the purpose of enhancing physical properties that the polyurethane aqueous dispersion is required to have, and imparting various physical properties: a flame retardant, a plasticizer, an antioxidant, an ultraviolet absorber, a light stabilizer, an emulsifier, an antifoam agent, a filler, an internal mold release agent, a reinforcer, a matting agent, a conductivity imparting agent, an electrification control agent, an antistatic agent, an antimicrobial agent, a leveling agent, a lubricant, and other processing aids.

The polyurethane aqueous dispersion of the present invention is produced through the steps of: producing an isocyanate group-terminated prepolymer (hereinafter referred to by abbreviation as "the prepolymer" in some cases) by causing the above-described components (A) to (E), and another component as required, to react; subsequently neutralizing the prepolymer; dispersing the obtained neutralized substance in water; and thereafter, causing chain extension reaction by using an amine-based chain extender (F).

An equivalent ratio of isocyanate group to hydroxyl group (NCO group/OH group) when the prepolymer is produced is not limited particularly; it is typically 1.05 to 2, and preferably 1.05 to 1.5.

Reaction conditions when the prepolymer is produced are not limited particularly; the prepolymer is produced under the conditions of typically 30 to 120° C., preferably 40 to 100° C., more preferably 45 to 90° C., and typically 1 to 10 hours. Here, a reaction catalyst such as dioctyltin dilaurate, dibutyltin dilaurate, stannous octoate, dibutyltin-2-ethyl hexoate, triethylamine, triethylenediamine, N-methylmorpholine, or the like can be added as required. One type of the above-described reaction catalyst can be used alone, or alternatively, two or more types of the same can be used in combination.

Further, at the stage of reaction, or after the completion of the reaction, an organic solvent that is not reactive with an isocyanate group can be added. Examples of such an organic solvent include acetone, methyl ethyl ketone, toluene, tetrahydrofuran, dioxane, N,N-dimethylformamide, and N-methylpyrrolidone. In the present invention, the method for producing the isocyanate group-terminated prepolymer is not limited particularly, and the one-shot method (one stage type), which is conventionally known, or a multistage isocyanate polyaddition reaction method, is used.

The prepolymer typically has an isocyanate value (a content by weight of residual isocyanate groups with respect to a resin solid content) of 0.1 to 5%.

The neutralizer used for neutralizing the prepolymer is not limited particularly as long as it can neutralize carboxyl groups. Examples of the neutralizer include: amines such as trimethylamine, triethylamine, tri-n-propylamine, tributylamine, and triethanolamine; sodium hydroxide; potassium hydroxide; and ammonia.

When the neutralized substance of the prepolymer is emulsified and dispersed in water, 50 to 600 parts by weight of water is used with respect to 100 parts by weight of a resin solid content in the prepolymer so that phase inversion emulsification efficiently proceeds.

A polyurethane aqueous dispersion is produced by adding the component (F) during emulsification or after emulsification so that a chain extension reaction is caused to occur. The amount of the component (F) used can be arbitrarily selected, in a range of 0.3 to 1.5 equivalent, preferably 0.4 to 1.2 equivalent, with respect to the terminal isocyanate groups of the prepolymer.

In the case where the polyurethane aqueous dispersion contains an organic solvent, the solvent is desirably distilled away under a reduced pressure, at 30 to 80° C. The concentration of a resin solid content (non-volatile content) in the polyurethane aqueous dispersion is preferably in a range of 15 to 66%. The concentration of the resin solid content in the polyurethane aqueous dispersion can also be adjusted by adding water or distilling water away.

In the present invention, the content of EO originating from ethylene oxide units (EO) in the polyurethane aqueous dispersion is not limited particularly, but from the viewpoint that a formed film obtained by salt coagulation method has practical utility in terms of moisture permeability, the content of EO is preferably 2.8% by weight or more, and more preferably 3.0% by weight or more, with respect to polyurethane (i.e., the resin solid content) in the polyurethane aqueous dispersion. In the present invention, "the moisture permeability of the formed film" is evaluated according to a degree of moisture permeability of a film produced by salt coagulation method (film thickness: about 100 μm) that is measured according to the JIS L 1099A-1 method (the calcium chloride method). The evaluation criteria are as follows: when the degree of moisture permeability is 550 $g/m^2$-24 hrs or more and less than 800 $g/m^2$-24 hrs, it is determined that the formed film has practical utility; when the degree of moisture permeability is 800 $g/m^2$-24 hrs or more, it is determined that the formed film has excellent practical utility. The moisture permeability is regarded as an index for non-stuffiness in the case where the formed film is worn for a long time.

Further, if the EO content is increased excessively, a formed film obtained by salt coagulation method has poor practical utility in terms of resistance against ethanol water. Therefore, in order that a formed film obtained by salt coagulation method should surely have practical utility in terms of resistance against ethanol water and moisture permeability, the EO content is preferably 2.8 to 14% by weight, and more preferably 7 to 14% by weight.

In order to set the EO content in the above-described range, the EO content can be adjusted by setting the charged raw materials in such a manner that the total weight of EO among the non-volatile production raw materials having EO units is in the above-described range of the content with respect to the total weight of the non-volatile production raw materials among the production raw materials of the polyurethane aqueous dispersion.

Further, in the present invention, the content of 2,4'-MDI in the MDIs containing at least 2,4'-MDI and 4,4'-MDI is set to preferably 40% by weight or more, more preferably 70% by weight or more, particularly preferably 80% by weight or more, whereby a formed film obtained by salt coagulation method has practical utility in terms of flexibility, and has practical utility in terms of the above-described processing suitability. In the present invention, "the flexibility of the formed film" is evaluated according to a 100 percent modulus that is measured in the following manner: from a film (film thickness: about 100 μm) produced by salt coagulation method, a test specimen is cut out using a JIS No. 3 dumbbell, and a 100 percent modulus is measured according to JIS K6251 using a tensile testing machine. The evaluation criteria are as follows: when the 100 percent modulus is 4.0 MPa or more, and less than 7.0 MPa, it is determined that the film has practical utility, and when the 100 percent modulus is less than 4.0 MPa, it is determined that the film has excellent practical utility. The flexibility of the formed film is regarded as an index for determining the fitting feel when the formed film is worn.

In order to enhance the practical utility in terms of the flexibility and the processing suitability of a formed film as described above using MDI having an increased content of 2,4'-MDI, it is not necessary particularly to set the EO content in the above-described range, but even in the case where the EO content is rather set lower than the above-described range, the above-described effects can be still exhibited. In this case, the EO content is typically in a range of 1 to 14% by weight for use, preferably in a range of 1 to 8% by weight, and further preferably in a range of 1 to 3% by weight. Further, in order to enhance practical utility of the formed film in terms of the flexibility and the processing suitability and ensure practical utility in terms of the resistance against ethanol water and the moisture permeability, the EO content is preferably in a range of 1 to 14% by weight, and more preferably in a range of 7 to 14% by weight.

The formed film of the present invention is produced using a polyurethane aqueous dispersion and a coagulant liquid in combination, by a forming method that is called salt coagulation method. More specifically, examples of the method include: a method in which a mold is immersed in a coagulant liquid so that a coagulated layer is formed on the mold, and is immersed in a polyurethane aqueous dispersion so that a coating is formed, and is dried; and a method in which a polyurethane aqueous dispersion is applied or the like to a mold so that a polyurethane aqueous dispersion layer is formed on the mold, and a coagulant liquid is applied or the like thereover so that a coating is formed, and is dried.

The coagulant liquid is a solution obtained by dissolving a coagulant in water or alcohol as a solvent. Examples of the coagulant used in the present invention include the following inorganic salts and acids. Examples of the inorganic salts include metal halides such as sodium chloride, calcium chloride, magnesium chloride, zinc chloride, and aluminum chloride; nitrates such as sodium nitrate, calcium nitrate, and zinc nitrate; acetates such as sodium acetate, calcium acetate, and zinc acetate; sulfates such as calcium sulfate, magnesium sulfate, and aluminum sulfate. Examples of the acid include formic acid, acetic acid, citric acid, and boric acid. Among the above-described coagulants, calcium nitrate is preferred since it has excellent coagulating properties and provides a coagulation effect in a short time. One of these coagulants is used alone, or two or more of the same are used in combination. A surfactant and a filler such as calcium carbonate or talc may be formulated with the coagulant liquid as required.

The mold used in the production is not limited particularly, and various types of molds that are conventionally known, for example, those made of ceramics, glass, metals and the like, can be used. The preheating temperature and the immersion time for the mold are set according to the composition of the aqueous polyurethane resin composition, the film thickness of the formed film, and the like; they are not limited particularly. Further, the forming temperature is not limited particularly, either, but in order to shorten the forming time, the forming temperature is preferably 100 to 200° C., and more preferably 110 to 200° C.

The film thickness of the formed film of the present invention is not limited particularly as it varies with the application purposes, but it is preferably 10 to 1000 μm, and more preferably 20 to 1000 μm.

The formed film of the present invention is applicable for gloves, finger stalls, condoms and the like, and particularly suitable for gloves.

Example

Hereinafter, the present invention is explained specifically based on experiment examples. The present invention, however, is not limited by these examples at all. It should be noted that "part(s)" and "%" in the descriptions of Examples mean "part(s) by weight" and "% by weight", respectively, unless otherwise provided specifically.

Hereinafter, production raw materials of the polyurethane aqueous dispersion, production examples of the polyurethane aqueous dispersion, formed film production examples using salt coagulation method, and evaluation methods for these are explained.

<Production Raw Materials of Polyurethane Aqueous Dispersion>

Component (A): Polyisocyanate diphenylmethane diisocyanate (the component (a1))
(Trade Name: "Millionate MT", produced by Nippon Polyurethane Industry Co., Ltd. It contains 99.5% or more of 4,4'-MDI, and the rest of 2,4'-MDI. Hereinafter, this is referred to by abbreviation as "MDI" in the case where it is not necessary to distinguish this product and other products of the component (a1) particularly. In the case where it is necessary to distinguish this product and other products of the component (a1), the trade name is described.)
(Trade Name: "Lupranate MI", produced by BASF INOAC Polyurethanes Ltd., 4,4'-MDI 2,4'-MDI=50%:50%)
(Trade Name: "Millionate NM100", produced by Nippon Polyurethane Industry Co., Ltd., 4,4'-MDI 2,4'-MDI=5 to 15%: 95 to 85%)

alicyclic diisocyanate (component (a2))
(hydrogenated diphenylmethane diisocyanate (Trade Name: "Desmodur W", produced by Sumika Bayer Urethane Co., Ltd., hereinafter referred to by abbreviation as "H12MDI"))
(isophorone diisocyanate (Trade Name: "Desmodur I", produced by Sumika Bayer Urethane Co., Ltd., hereinafter referred to by abbreviation as "IPDI"))

Component (B): random copolymer of ethylene oxide and tetrahydrofuran (hereinafter referred to by abbreviation as "EO/THF random copolymer")

Trade Name: "Polyserine DC3000E", molar ratio (EO/THF)=50/50, number average molecular weight: 3100, produced by NOF Corporation, hereinafter referred to by abbreviation as "DC3000")

Trade Name: "polyserine DC1800E", molar ratio (EO/THF)=50/50, number average molecular weight: 1800, produced by NOF Corporation, hereinafter referred to by abbreviation as "DC 1800")

Trade Name: "polyserine DC1100E", molar ratio (EO/THF)=65/35, number average molecular weight: 1050, produced by NOF Corporation, hereinafter referred to by abbreviation as "DC1100")

Component (C): Polyol polyhexamethylene carbonate diol (Trade Name: "UH-300", number average molecular weight: 3000, produced by Ube Industries, Ltd., hereinafter referred to by abbreviation as "UH300")

polytetramethylene glycol (Trade Name: "PTG-2900", number average molecular weight: 2900, produced by Hodogaya Chemical Co., Ltd., hereinafter referred to by abbreviation as "PTG2900")

polyethylene glycol (Trade Name: "PEG2000", number average molecular weight: 2000, produced by NOF Corporation, hereinafter referred to by abbreviation as "PEG2000")

polyester polyol (Trade Name: "HOKOKUOL HT-300", polyester polyol obtained by condensation polymerization of 1,4-butanediol and adipic acid, number average molecular weight: 3000, produced by Hokoku Corp., hereinafter referred to by abbreviation as "HT300")

polyester polyol (Trade Name: "Nipporan 4042", polyester polyol obtained by condensation polymerization of 1,4-butanediol, ethylene glycol and adipic acid, number average molecular weight: 2000, produced by Nippon Polyurethane Industry Co., Ltd.)

Component (D): Polyhydric Alcohol-Based Chain Extender 1,4-butanediol

Component (E): diol compound having a carboxyl group
2,2-dimethylol propionic acid (hereinafter referred to by abbreviation as "DMPA")
2,2-dimethylol butanoic acid (hereinafter referred to by abbreviation as "DMBA")

Component (F): amine-based chain extender
30% piperazine hexahydrate

Other Components
water
neutralizer: triethylamine
solvent: N-methylpyrrolidone (NMP), methyl ethyl ketone (MEK)
catalyst: dioctyltin dilaurate <Evaluation of Processing Performance of Salt Coagulation Method>

The evaluation items include gelation performance, gelation strength, and film forming performance.

Gelation Performance

A plate made of ceramic (hereinafter referred to by abbreviation as "ceramic plate") in a size of vertical 180 mm×horizontal 70 mm was immersed in an aqueous solution of calcium nitrate having a concentration of 10% at a speed of 5 mm/sec in such a manner that the ceramic plate was immersed for 100 mm in the vertical direction, and subsequently the ceramic plate was picked up out of the solution at a speed of 10 mm/sec. Thereafter, the ceramic plate was dried by heating in an oven at 100° C. Through this step, on the immersed portion (vertical 100 mm×horizontal 70 mm) of the ceramic plate, which was immersed in the aqueous calcium nitrate solution, a calcium nitrate layer was formed. Subsequently, the ceramic plate, cooled to 55° C.±5° C., was immersed in a polyurethane aqueous dispersion at a speed of 5 mm/sec until the part of 100 mm in the vertical direction was immersed so that the entirety of the calcium nitrate layer formed on the ceramic plate was immersed therein, then left to stand for 30 seconds, and it was pulled up at a speed of 10 mm/sec. In this series of steps, a gel coating of the polyurethane aqueous dispersion, which was gelled by salt coagulation method, was formed on the surface of the ceramic plate.

Subsequently, the ceramic plate was left to stand still at room temperature of 23±2° C. for one minute in a state in which a shorter side portion thereof that was immersed in both of the aqueous solution of calcium nitrate and the polyurethane aqueous dispersion was positioned on the upper side. An appearance of the gel coating was observed by visual observation, and gelation performance was evaluated according to the following criteria.

◎: no crack occurred to the coating (good)
○: one or two cracks of smaller than 1 mm occurred to the coating, but no crack of 1 mm or greater occurred (slightly good)
X: three or more cracks of smaller than 1 mm occurred to the gel coating, or alternatively, one or more cracks of 1 mm or greater occurred (poor)
*Among the above-described criteria, "◎" and "○" are evaluated as having practical utility.

Gelation Strength

When gelation performance was evaluated, the coating was peeled from the ceramic plate, and was pulled by fingers, whereby the gelation strength thereof (state of coating strength of the gel coating) was evaluated according to the following criteria.
◎: a coating was formed, and the coating had rubber elasticity (stretchability) (good)
○: a coating was formed, and the coating became elongated (slightly good)
X: a coating was formed but the coating could not be elongated, or no coating was formed (poor)
*Among the above-described criteria, "◎" and "○" are evaluated as having practical utility.

Film Forming Performance

The gel coating-formed ceramic plate, which was used in the above-described evaluation of "Gelation Performance", was dried by heating in an oven at 120° C. for 30 minutes, and the state of the coating therein was observed by visual observation. The film forming performance was evaluated according to the criteria shown below.
◎: no crack occurred to the coating (good)
○: one or two cracks of smaller than 1 mm occurred to the coating, but no crack of 1 mm or greater occurred (slightly good)
X: three or more cracks of smaller than 1 mm occurred to the gel coating, or alternatively, one or more cracks of 1 mm or greater occurred (poor)

*Among the above-described criteria, "◎" and "○" are evaluated as having practical utility.

Flexibility:
Measurement of 100 Percent Modulus

From the dried coating used in the above-described evaluation of "Film Forming Performance" (the coating obtained by drying the gel coating (hereinafter referred to by abbreviation as "dried coating"), thickness: 100 μm), test specimens were cut out using a JIS No. 3 dumbbell. The specimens were evaluated according to JIS K6251 by using a tensile testing machine LR-5K manufactured by Lloyd Instruments Ltd., under the following conditions: chuck interval: 60 mm, mark line: 20 mm, tensile speed: 500 mm/min, temperature: 23±2° C.

Tensile loads when test specimens became elongated by 100% were measured, and tensile strengths were determined by the following formula:

$$100 \text{ percent modulus(MPa)} = F_{100\%}/A$$

where "$F_{100\%}$" represents a tensile load (N) when a specimen was elongated by 100%, and "A" represents an area (mm$^2$) of a cross section of a test specimen.

The evaluation criteria for the 100 percent modulus are as follows:
◎: less than 4.0 MPa (good)
○: 4.0 MPa or more, and less than 7.0 MPa (slightly good)
X: 7.0 MPa or more (poor)
*Among the above-described criteria, "◎" and "○" are evaluated as having practical utility.

Resistance Against Ethanol Water:
Measurement of Tensile Strength

From the dried coating (thickness: 100 μm) used in the above-described evaluation of the "Film Forming Performance", test specimens were cut out using a JIS No. 3 dumbbell. The specimens were immersed in a 70% aqueous solution of ethyl alcohol (23° C.±2° C.) for 30 minutes, and thereafter, they were taken out therefrom. The test specimens thus taken out were wiped lightly, and 90 seconds after, a tensile strength test was performed according to JIS K-6301. Resistance against ethanol water was evaluated according to the following criteria:
◎: tensile strength is 10 MPa or more (good)
○: tensile strength is 4 MPa or more, and less than 10 MPa (slightly good)
X: tensile strength was less than 4 MPa (poor)
*Among the above-described criteria, "◎" and "○" are evaluated as having practical utility.

Moisture Permeability:
Measurement of Degree of Moisture Permeability

Degrees of moisture permeability of the dried coatings (thickness:100 μm) used in the above-described evaluation of the "Film Forming Performance" were measured according to the JIS L 1099A-1 method (calcium chloride method). Moisture permeability was evaluated according to the following criteria:
◎: 800 g/m$^2$-24 hrs or more
○: 550 g/m$^2$-24 hrs or more, and less than 800 g/m$^2$-24 hrs
X: less than 550 g/m$^2$-24 hrs
*Among the above-described criteria, "◎" and "○" are evaluated as having practical utility.

1. Study about Preferable Polyol
Production of Polyurethane Aqueous Dispersion No. 1

In a reactor, 24.9 parts of DC3000 (the component (B)), 158.4 parts of UH300 (the component (C)), and 0.01 parts of dioctyltin dilaurate were charged, and they were agitated and dissolved sufficiently. 25.2 parts of MDI (the component (A)) and 26.4 parts of H12MDI (the component (A)) were added thereto and were caused to react at 85° C. for 3 hours. Next, after it was cooled to 60° C., 5.0 parts of DMPA (the component (E)), 5.2 parts of 1,4-butanediol (the component (D)), 61.3 parts of NMP, and 188.7 parts of MEK were added thereto, and agitated and dissolved sufficiently. Then, 0.04 parts of dioctyltin dilaurate was added thereto, and they were caused to react at 80° C. for 8 hours. As a result, a prepolymer having an isocyanate value (content by weight of residual isocyanate groups with respect to a solid content) of 0.8% was obtained. This prepolymer was cooled to 50° C., and 3.8 parts of triethylamine was added for neutralization, and subsequently, 470.8 parts of water was added, so that phase inversion emulsification occurred. To this emulsification dispersion liquid, 18.9 parts of 30% piperazine hexahydrate (the component (F)) (100 equivalent % with respect to residual isocyanate groups in terms of amine groups) was added, so that the liquid was emulsified and dispersed. Solvent was removed from the obtained emulsified liquid, whereby a polyurethane aqueous dispersion No. 1 having a non-volatile content of 25% and pH 7.3 was obtained.

Production of Polyurethane Aqueous Dispersions No. 2 to No. 9

Polyurethane aqueous dispersions No. 2 to No. 9 were produced with raw materials and formulations shown in Table 1, by the same method as that for the polyurethane aqueous dispersion No. 1.

With regard to the polyurethane aqueous dispersions No. 1 to No. 9, processing performance was evaluated by the method explained in the section of <Evaluation of Processing Performance of Salt Coagulation Method>. With regard to the obtained dried coatings, flexibility and resistance against ethanol water were evaluated. The results are shown in Table 2. It should be noted that numerical values of charged raw materials in Table 2 represent contents (% by weight) of respective essential components (A) to (F) in the case where a total amount of the essential components (A) to (F), among the production raw materials, is assumed to be 100%.

TABLE 1

| Charged Raw Material (parts by weight) | No. 1 | No. 2 | No. 3 | No. 4 | No. 5 | No. 6 | No. 7 | No. 8 | No. 9 |
|---|---|---|---|---|---|---|---|---|---|
| Polyisocyanate (A) | | | | | | | | | |
| MDI (a1) | 25.2 | 25.2 | 25.4 | 25.3 | 25.2 | 25.5 | 25.2 | 25.0 | 25.0 |
| H12MDI (a2) | 26.4 | 26.4 | 26.6 | 26.5 | 26.4 | 26.7 | 26.4 | 26.2 | 26.3 |
| EO/THF random copolymer (B) | | | | | | | | | |
| DC3000 | 24.9 | | | | | | | | |
| DC1800 | | 19.0 | | | | | | | |
| DC1100 | | | 24.5 | | | | | | |
| Polyol (C) | | | | | | | | | |
| UH300 | 158.4 | 164.7 | 159.7 | 183.1 | | | | 159.1 | 174.3 |
| HT300 | | | | | 183.2 | | | | |
| Nipporan 4042 | | | | | | 185.4 | | | |
| PTG2900 | | | | | | | 183.5 | 24.7 | |
| PEG2000 | | | | | | | | | 9.5 |
| 1,4-butandiol (D) | 5.2 | 4.8 | 3.9 | 5.3 | 5.2 | 2.5 | 5.1 | 5.1 | 5.0 |
| DMPA (E) | 5.0 | 5.0 | 5.0 | 5.0 | 5.0 | 5.0 | 4.9 | 5.0 | 5.0 |
| 30% piperazine hexahydrate (F) | 18.9 | 19.6 | 20.6 | 19.8 | 23.4 | 23.6 | 24.4 | 19.1 | 20.6 |
| Triethylamine | 3.8 | 3.8 | 3.8 | 3.7 | 3.7 | 3.8 | 3.7 | 3.7 | 3.7 |
| NMP | 61.3 | 61.3 | 61.3 | 61.3 | 61.3 | 61.3 | 61.3 | 61.3 | 61.3 |
| MEK | 188.7 | 188.7 | 188.7 | 188.7 | 188.7 | 188.7 | 188.7 | 188.7 | 188.7 |
| Water | 470.8 | 470.8 | 470.6 | 470.8 | 470.6 | 470.5 | 470.8 | 471.0 | 470.8 |

TABLE 2

| Charged Raw Material (wt %) | No. 1 | No. 2 | No. 3 | No. 4 | No. 5 | No. 6 | No. 7 | No. 8 | No. 9 |
|---|---|---|---|---|---|---|---|---|---|
| Polyisocyanate (A) | | | | | | | | | |
| MDI (a1) | 10.2 | 10.2 | 10.2 | 10.2 | 10.2 | 10.3 | 10.1 | 10.1 | 10.1 |
| H12MDI (a2) | 10.6 | 10.7 | 10.7 | 10.7 | 10.7 | 10.8 | 10.6 | 10.6 | 10.6 |
| a1/a2 (molar ratio) | 50/50 | 50/50 | 50/50 | 50/50 | 50/50 | 50/50 | 50/50 | 50/50 | 50/50 |
| EO/THF random copolymer (B) | | | | | | | | | |
| DC3000 | 10.1 | | | | | | | | |
| DC1800 | | 7.7 | | | | | | | |
| DC1100 | | | 9.9 | | | | | | |
| Polyol (C) | | | | | | | | | |
| UH300 | 64.0 | 66.5 | 64.5 | 73.9 | | | | 64.3 | 70.3 |
| HT300 | | | | | 73.8 | | | | |
| Nipporan 4042 | | | | | | 74.7 | | | |
| PTG2900 | | | | | | | 73.9 | 10.0 | |
| PEG2000 | | | | | | | | | 3.8 |

TABLE 2-continued

| Charged Raw Material (wt %) | No. 1 | No. 2 | No. 3 | No. 4 | No. 5 | No. 6 | No. 7 | No. 8 | No. 9 |
|---|---|---|---|---|---|---|---|---|---|
| 1,4-butandiol (D) | 2.1 | 1.9 | 1.6 | 2.1 | 2.1 | 1.0 | 2.1 | 2.1 | 2.0 |
| DMPA (E) | 2.0 | 2.0 | 2.0 | 2.0 | 2.0 | 2.0 | 2.0 | 2.0 | 2.0 |
| Piperazine (F) | 1.0 | 1.1 | 1.1 | 1.1 | 1.3 | 1.3 | 1.3 | 1.0 | 1.1 |
| <Polyurethane aqueous dispersion> | | | | | | | | | |
| Emulsification state | Good | Good | Good | Good | Good | Good | Good | Good | Good |
| Non-volatile content (wt %) | 25 | 25 | 25 | 25 | 25 | 25 | 25 | 25 | 25 |
| EO content (wt %) | 3.8 | 2.9 | 5.3 | | | | | | 3.8 |
| <Film obtained by Salt Coagulation Method> (Flexibility) | | | | | | | | | |
| 100% modulus (MPa) | 4.5 | 4.0 | 4.0 | 7.5 | 4.9 | 4.6 | 3.0 | 7.5 | 7.0 |
| Evaluation (Resistance against ethanol water) | ○ | ○ | ○ | X | ○ | ○ | ○ | X | X |
| Tensile strength (MPa) | 5.9 | 5.2 | 5.2 | 12 | 11.2 | 1.6 | 9.1 | 7.0 | 7.7 |
| Evaluation (Processing performance) | ○ | ○ | ○ | ◎ | ◎ | X | ○ | ○ | ○ |
| Gelation performance | ◎ | ◎ | ◎ | ◎ | ◎ | X | ◎ | ◎ | ◎ |
| Gelation strength | ○ | ○ | ○ | X | X | X | X | X | X |
| Film forming performance | ◎ | ◎ | ◎ | X | ◎ | ◎ | X | X | X |

The polyurethane aqueous dispersions No. 1 to No. 3 in which the component (B) and the component (C) were used in combination as the polyol exhibited gelation strengths that were evaluated as being "slightly good", and resistances against ethanol water that were also evaluated as being "slightly good", therefore having practical utility in terms of both of the two items. On the other hand, among the polyurethane aqueous dispersions No. 4 to No. 7 in which only one type of polyol, i.e., only the component (C), was used, some specimens (No. 4, No. 5) exhibited resistance against ethanol water that were evaluated as being "good", but their gelation strengths were evaluated as being "poor". Thus, no specimen was evaluated to have practical utility in terms of both of the two items. Further, the polyurethane aqueous dispersions No. 8 and No. 9 in which two types of the components (C) were used as polyol exhibited resistances against ethanol water that were evaluated to be "slightly good", but their gelation strengths were evaluated to be "poor". Thus, no specimen was evaluated to have practical utility in terms of both of the two items. From the above-described results, it can be considered that it is necessary to use the component (B) and the component (C) in combination as polyol in order to provide a polyurethane aqueous dispersion that has practical utility in terms of both of the gelation strength and the resistance against ethanol water.

2. Characteristics of Polyurethane Aqueous Dispersion in which MDI and Alicyclic Diisocyanate are Used in Combination Production of Polyurethane Aqueous Dispersion No. 10

In a reactor, 12.8 parts of DC3000 (the component (B)), 170.9 parts of UH-300 (the component (C)), and 0.01 parts of dioctyltin dilaurate were charged, and agitated and dissolved sufficiently. Then, 33.6 parts of MDI (the component (A)), and 17.6 parts of H12MDI (the component (A)) were added thereto, and they were caused to react at 85° C. for 3 hours. Next, after it was cooled to 60° C., 5.0 parts of DMPA (the component (E)), 5.3 parts of 1,4-butanediol (the component (D)), 61.3 parts of NMP, and 188.7 parts of MEK were added thereto, and agitated and dissolved sufficiently. Then, 0.04 parts of dioctyltin dilaurate was added thereto, and they were caused to react at 80° C. for 8 hours. As a result, a prepolymer having an isocyanate value (content by weight of residual isocyanate groups with respect to a solid content) of 0.8% was obtained. This prepolymer was cooled to 50° C., and 3.7 parts of triethylamine was added for neutralization, and subsequently, 470.9 parts of water was added, so that phase inversion emulsification occurred. To this emulsification dispersion liquid, 19.1 parts of 30% piperazine hexahydrate (the component (F)) (100 equivalent % with respect to residual isocyanate groups in terms of amine groups) was added, so that the liquid was emulsified and dispersed. Solvent was removed from the obtained emulsified liquid, whereby a polyurethane aqueous dispersion No. 10 having a non-volatile content of 25% and pH 7.3 was obtained.

Production of Polyurethane Aqueous Dispersions No. 11 to No. 18

Polyurethane aqueous dispersions No. 11 to No. 18 were produced with raw materials and formulations shown in Table 3, by the same method as that for the polyurethane aqueous dispersion No. 10.

With regard to the polyurethane aqueous dispersions No. 10 to No. 18, processing performance was evaluated by the method explained in the section of <Evaluation of Processing Performance of Salt Coagulation Method>. With regard to the obtained dried coatings, flexibility and resistance against ethanol water were evaluated. The results are shown in Table 4. It should be noted that numerical values of charged raw materials in Table 4 represent contents (% by weight) of respective essential components (A) to (F) in the case where a total amount of the essential components (A) to (F), among the production raw materials, is assumed to be 100%.

TABLE 3

| Charged Raw Material (parts by weight) | No. 10 | No. 11 | No. 12 | No. 13 | No. 14 | No. 15 | No. 16 | No. 17 | No. 18 |
|---|---|---|---|---|---|---|---|---|---|
| Polyisocyanate (A) | | | | | | | | | |
| MDI (a1) | 33.6 | 33.5 | 25.2 | 18.9 | 12.6 | 50.6 | | 25.6 | |
| H12MDI (a2) | 17.6 | 17.7 | 26.4 | 32.9 | 39.5 | | 52.5 | | |
| IPDI (a2) | | | | | | | | 22.7 | 46.0 |
| DC3000 (B) | 12.8 | 12.8 | 12.8 | 12.8 | 12.8 | 12.9 | 12.7 | 13.0 | 13.2 |
| UH300 (C) | 170.9 | 170.8 | 170.6 | 170.4 | 170.2 | 171.4 | 169.8 | 173.4 | 175.4 |
| 1,4-butandiol (D) | 5.3 | 7.0 | 5.2 | 5.3 | 5.3 | 5.3 | 5.2 | 5.4 | 5.5 |
| DMPA (E) | 5.0 | 4.9 | 5.0 | 4.9 | 4.9 | 5.0 | 4.9 | 5.0 | 5.0 |
| 30% piperazine hexahydrate (F) | 19.1 | 11.0 | 19.5 | 20.8 | 21.9 | 20.8 | 21.7 | 19.8 | 23.4 |
| Triethylamine | 3.7 | 3.7 | 3.8 | 3.7 | 3.7 | 3.7 | 3.7 | 3.7 | 3.8 |
| NMP | 61.3 | 61.7 | 61.3 | 61.3 | 61.3 | 61.3 | 61.3 | 61.3 | 61.3 |
| MEK | 188.7 | 188.3 | 188.7 | 188.7 | 188.7 | 188.7 | 188.7 | 188.7 | 188.7 |
| Water | 470.9 | 481.9 | 470.9 | 471.1 | 471.1 | 470.8 | 471.1 | 470.6 | 470.3 |

TABLE 4

| | No. 10 | No. 11 | No. 12 | No. 13 | No. 14 | No. 15 | No. 16 | No. 17 | No. 18 |
|---|---|---|---|---|---|---|---|---|---|
| <Charged Raw Material (wt %)> | | | | | | | | | |
| Polyisocyanate (A) | | | | | | | | | |
| MDI (a1) | 13.6 | 13.5 | 10.2 | 7.6 | 5.1 | 20.4 | | 10.3 | |
| H12MDI (a2) | 7.1 | 7.1 | 10.6 | 13.3 | 15.9 | | 21.2 | | |
| IPDI (a) | | | | | | | | 9.2 | 18.5 |
| a1/a2 (molar ratio) | 67/33 | 66/34 | 50/50 | 38/62 | 25/75 | 100/0 | 0/100 | 50/50 | 0/100 |
| DC3000 (B) | 5.2 | 5.2 | 5.2 | 5.2 | 5.1 | 5.2 | 5.1 | 5.2 | 5.3 |
| UH300 (C) | 69.0 | 68.8 | 68.9 | 68.7 | 68.6 | 69.2 | 68.4 | 70.0 | 70.7 |
| 1,4-butandiol (D) | 2.1 | 2.8 | 2.1 | 2.1 | 2.1 | 2.1 | 2.1 | 2.2 | 2.2 |
| DMPA (E) | 2.0 | 2.0 | 2.0 | 2.0 | 2.0 | 2.0 | 2.0 | 2.0 | 2.0 |
| Piperazine (F) | 1.0 | 0.6 | 1 | 1.1 | 1.2 | 1.1 | 1.2 | 1.1 | 1.3 |
| <Polyurethane aqueous dispersion> | | | | | | | | | |
| Emulsification state | Good | Good | Good | Good | Good | Not emulsified | Good | Good | Good |
| Non-volatile content (wt %) | 25 | 25 | 25 | 25 | 25 | — | 25 | 25 | 25 |
| EO content (wt %) | 2 | 2 | 2 | 2 | 1.9 | 2 | 1.9 | 2 | 2 |
| <Film obtained by Salt Coagulation Method> (Flexibility) | | | | | | | | | |
| 100% modulus (MPa) | 6.8 | 3.8 | 6.3 | 6.1 | 6 | — | 5.6 | 4.7 | 5.2 |
| Evaluation (Resistance against ethanol water) | ○ | ○ | ○ | ○ | ○ | | ○ | ○ | ○ |
| Tensile strength (MPa) | 10.8 | 5.8 | 11 | 6.8 | 4.5 | — | 1.3 | 5.9 | 1.9 |
| Evaluation (Processing performance) | ◎ | ○ | ◎ | ○ | ○ | — | X | ○ | X |
| Gelation performance | ◎ | ◎ | ◎ | ◎ | ◎ | — | ◎ | ◎ | ◎ |
| Gelation strength | ○ | ○ | ○ | ○ | ○ | — | ○ | ○ | ○ |
| Film forming performance | ◎ | ◎ | ◎ | ◎ | ◎ | — | ◎ | ◎ | ◎ |

This experiment was performed for particularly studying the relationship between the gelation strength and the resistance against ethanol water, with regard to coatings produced by salt coagulation method from polyurethane aqueous dispersions that were produced with the type and combination of the component (A) being varied, on the premise that the component (B) and the component (C) are used in combination as polyol.

In the case of No. 15 in which only MDI was used as the component (A), a polyurethane aqueous dispersion was not produced in the first place. In the cases of No. 16 and No. 18 in which either H12MDI or IPDI was used as the component (A), they were evaluated to have practical utility in terms of the gelation strength, but were not evaluated to have practical utility in terms of the resistance against ethanol water.

On the other hand, in the cases of No. 10 to 14 in which MDI and H12MDI were used in combination as the component (A), and in the case of No. 17 in which MDI and IPDI were used in combination as the component (A), they were evaluated to have practical utility in terms of both of the gelation strength and the anti-ethanol performance.

3. Study about Formulation that Provides Excellent Resistance Against Ethanol Water and Excellent Moisture Permeability Production of Polyurethane Aqueous Dispersion No. 19

In a reactor, 12.8 parts of DC3000 (the component (B)), 170.6 parts of UH-300 (the component (C)), and 0.01 parts of dioctyltin dilaurate were charged, and agitated and dissolved sufficiently. Then, 25.2 parts of MDI (the component (A)), and 26.4 parts of H12MDI (the component (A)) were added thereto, and they were caused to react at 85° C. for 3 hours. Next, after it was cooled to 60° C., 5.0 parts of DMPA (the component (E)), 5.2 parts of 1,4-butanediol (the component (D)), 61.3 parts of NMP, and 188.7 parts of MEK were added thereto, and agitated and dissolved sufficiently. Then, 0.04 parts of dioctyltin dilaurate was added thereto, and they were caused to react at 80° C. for 8 hours. As a result, a prepolymer having an isocyanate value (content by weight of residual isocyanate groups with respect to a solid content) of 0.8% was obtained. This prepolymer was cooled to 50° C., and 3.8 parts of triethylamine was added for neutralization, and subsequently, 470.9 parts of water was added, so that phase inversion emulsification occurred. To this emulsification dispersion liquid, 19.5 parts of 30% piperazine hexahydrate (the component (F)) (100 equivalent % with respect to residual isocyanate groups in terms of amine groups) was added, so that the liquid was emulsified and dispersed. Solvent was removed from the obtained emulsified liquid, whereby a polyurethane aqueous dispersion No. 19 having a non-volatile content of 25% and pH 7.3 was obtained.

Production of Polyurethane Aqueous Dispersions No. 20 to No. 27

Polyurethane aqueous dispersions No. 20 to No. 27 were produced with raw materials and formulations shown in Table 5, by the same method as that for the polyurethane aqueous dispersion No. 19.

With regard to the polyurethane aqueous dispersions No. 19 to No. 27, processing performance was evaluated by the method explained in the section of <Evaluation of Processing Performance of Salt Coagulation Method>. With regard to the obtained dried coatings, flexibility, resistance against ethanol water, and moisture permeability were evaluated. The results are shown in Table 6. It should be noted that numerical values of charged raw materials in Table 6 represent contents (% by weight) of respective essential components (A) to (F) in the case where a total amount of the essential components (A) to (F), among the production raw materials, is assumed to be 100%.

TABLE 5

| Charged Raw Material (parts by weight) | No. 4 | No. 19 | No. 1 | No. 20 | No. 21 | No. 22 | No. 23 | No. 24 | No. 25 | No. 26 | No. 27 |
| --- | --- | --- | --- | --- | --- | --- | --- | --- | --- | --- | --- |
| Polyisocyanate (A) | | | | | | | | | | | |
| MDI (a1) | 25.3 | 25.2 | 25.2 | 25.1 | 25.0 | 25.1 | 25.0 | 12.5 | 25.1 | 25.1 | 25.1 |
| H12MDI (a2) | 26.5 | 26.4 | 26.4 | 26.3 | 26.2 | 26.3 | 26.2 | 39.3 | 26.3 | 26.3 | 26.3 |
| DC3000 (B) | | 12.8 | 24.9 | 51.4 | 77.6 | 102.6 | 128.6 | 77.4 | 77.2 | 77.2 | 77.2 |
| UH300 (C) | 183.1 | 170.6 | 158.4 | 132.3 | 106.3 | 81.2 | 55.5 | 106.1 | 106.6 | 106.6 | 106.6 |
| 1,4-butanediol (D) | 5.3 | 5.2 | 5.2 | 5.7 | 5.7 | 5.7 | 5.7 | 5.7 | 5.3 | 4.8 | 4.4 |
| DMPA (E) | 5.0 | 5.0 | 5.0 | 4.2 | 4.2 | 4.2 | 4.3 | 4.2 | 4.2 | 4.2 | 4.2 |
| 30% piperazine hexahydrate (F) | 19.8 | 19.5 | 18.9 | 21.5 | 20.0 | 20.8 | 21.0 | 21.7 | 20.0 | 26.0 | 29.5 |
| Triethylamine | 3.7 | 3.8 | 3.8 | 3.2 | 3.2 | 3.2 | 3.2 | 3.2 | 3.2 | 3.2 | 3.2 |
| NMP | 71.3 | 61.3 | 61.3 | 61.3 | 61.3 | 61.3 | 61.3 | 61.3 | 61.2 | 61.0 | 61.0 |
| MEK | 188.7 | 188.7 | 188.7 | 188.7 | 188.7 | 188.7 | 188.7 | 188.7 | 188.8 | 189.0 | 189.0 |
| Water | 470.8 | 470.9 | 470.8 | 471.4 | 471.5 | 471.5 | 471.4 | 471.5 | 468.7 | 465.8 | 463.0 |

TABLE 6

| Charged Raw Material (wt %) | No. 4 | No. 19 | No. 1 | No. 20 | No. 21 | No. 22 | No. 23 | No. 24 | No. 25 | No. 26 | No. 27 |
| --- | --- | --- | --- | --- | --- | --- | --- | --- | --- | --- | --- |
| Polyisocyanate (A) | | | | | | | | | | | |
| MDI (a1) | 10.2 | 10.2 | 10.2 | 10.1 | 10.1 | 10.1 | 10.1 | 5.0 | 10.1 | 10.1 | 10.1 |
| H12MDI (a2) | 10.7 | 10.6 | 10.6 | 10.6 | 10.6 | 10.6 | 10.6 | 15.8 | 10.6 | 10.6 | 10.6 |
| a1/a2 (molar ratio) | 50/50 | 50/50 | 50/50 | 50/50 | 50/50 | 50/50 | 50/50 | 25/75 | 50/50 | 50/50 | 50/50 |
| DC3000 (B) | | 5.2 | 10.1 | 20.7 | 31.3 | 41.4 | 51.9 | 31.2 | 31.2 | 31.2 | 31.2 |
| UH300 (C) | 73.9 | 68.9 | 64.0 | 53.4 | 42.9 | 32.8 | 22.4 | 42.8 | 43.1 | 43.0 | 43.0 |
| 1,4-butandiol (D) | 2.1 | 2.1 | 2.1 | 2.3 | 2.3 | 2.3 | 2.3 | 2.3 | 2.1 | 1.9 | 1.8 |
| DMPA (E) | 2.0 | 2.0 | 2.0 | 1.7 | 1.7 | 1.7 | 1.7 | 1.7 | 1.7 | 1.7 | 1.7 |
| Piperazine (F) | 1.1 | 1.0 | 1.0 | 1.2 | 1.1 | 1.1 | 1.1 | 1.2 | 1.1 | 1.4 | 1.6 |
| <Polyurethane aqueous dispersion> | | | | | | | | | | | |
| Emulsification state | Good | Good | Good | Good | Good | Good | Good | Good | Good | Good | Good |
| Non-volatile content (wt %) | 25 | 25 | 25 | 25 | 25 | 25 | 25 | 25 | 25 | 25 | 25 |
| EO content (wt %) | 0 | 2.0 | 3.8 | 7.9 | 11.9 | 15.7 | 19.7 | 11.8 | 11.8 | 11.8 | 11.8 |

TABLE 6-continued

| Charged Raw Material (wt %) | No. 4 | No. 19 | No. 1 | No. 20 | No. 21 | No. 22 | No. 23 | No. 24 | No. 25 | No. 26 | No. 27 |
|---|---|---|---|---|---|---|---|---|---|---|---|
| <Film obtained by Salt Coagulation Method> (Flexibility) | | | | | | | | | | | |
| 100% modulus (MPa) | 7.5 | 6.3 | 4.5 | 4.3 | 3.9 | 3 | 3.2 | 4 | 3.8 | 4.1 | 5.3 |
| Evaluation (Resistance against ethanol water) | X | ○ | ○ | ○ | ◎ | ◎ | ◎ | ○ | ◎ | ○ | ○ |
| Tensile strength (MPa) | 12 | 11 | 5.9 | 10.2 | 5.5 | 0.5 | 0.3 | 1.8 | 5.5 | 5.9 | 5.4 |
| Evaluation (Moisture permeability) | ◎ | ◎ | ○ | ◎ | ○ | X | X | X | ○ | ○ | ○ |
| Degree of moisture permeability (g/m²-24 hrs) | 340 | 520 | 590 | 900 | 1050 | 1250 | 1390 | 1050 | 1060 | 1050 | 1050 |
| Evaluation (Processing performance) | X | X | ○ | ◎ | ◎ | ◎ | ◎ | ◎ | ◎ | ◎ | ◎ |
| Gelation performance | ◎ | ◎ | ◎ | ◎ | ◎ | ◎ | ◎ | ◎ | ◎ | ◎ | ◎ |
| Gelation strength | X | ○ | ○ | ○ | ◎ | ◎ | ○ | ○ | ○ | ○ | ○ |
| Film forming performance | X | ◎ | ◎ | ◎ | ◎ | ◎ | ◎ | ◎ | ◎ | ◎ | ○ |

This experiment was performed for studying the relationship between the content of ethylene oxide units (EO) (unit: % by weight)(hereinafter referred to by abbreviation as "EO content") with respect to polyurethane (resin solid content) in the polyurethane aqueous dispersion on one hand, and particularly the resistance against ethanol water and the moisture permeability on the other hand.

As is clear from Table 6, the specimens were evaluated to have practical utility in terms of the moisture permeability when the EO content was 2.8% by weight or more, and there was a tendency that the moisture permeability was enhanced as the EO content further increased.

Further, it was proved that though the practical utility was evaluated to be exhibited in terms of the resistance against ethanol water in usual cases, the practical utility was lost as the EO content increased excessively and became over 14% by weight.

4. Study about Formulation that Provides Excellent Flexibility and Excellent Gelation Strength Production of Polyurethane Aqueous Dispersion No. 28

In a reactor, 180.5 parts of DC3000 (the component (B)), 12.8 parts of UH-300 (the component (C)), and 0.01 parts of dioctyltin dilaurate were charged, and agitated and dissolved sufficiently. Then, 29.0 parts of Lupranate MI (the component (A)), and 15.3 parts of H12MDI (the component (A)) were added thereto, and they were caused to react at 85° C. for 3 hours. Next, after it was cooled to 60° C., 5.0 parts of DMPA (the component (E)), 3.1 parts of 1,4-butanediol (the component (D)), 61.4 parts of NMP, and 313.6 parts of MEK were added thereto, and agitated and dissolved sufficiently. Then, 0.04 parts of dioctyltin dilaurate was added thereto, and they were caused to react at 80° C. for 8 hours. As a result, a prepolymer having an isocyanate value (content by weight of residual isocyanate groups with respect to a solid content) of 0.9% was obtained. This prepolymer was cooled to 50° C., and 3.7 parts of triethylamine was added for neutralization, and subsequently, 474.7 parts of water was added, so that phase inversion emulsification occurred. To this emulsification dispersion liquid, 19.9 parts of 30% piperazine hexahydrate (the component (F)) (100 equivalent % with respect to residual isocyanate groups in terms of amine groups) was added, so that the liquid was emulsified and dispersed. Solvent was removed from the obtained emulsified liquid, whereby a polyurethane aqueous dispersion No. 28 having a non-volatile content of 25% and pH 7.3 was obtained.

Production of Polyurethane Aqueous Dispersions No. 29 and No. 30

Polyurethane aqueous dispersions No. 29 and No. 30 were produced with raw materials and formulations shown in Table 7, by the same method as that for the polyurethane aqueous dispersion No. 28.

With regard to the polyurethane aqueous dispersions No. 28 to No. 30, processing performance was evaluated by the method explained in the section of <Evaluation of Processing Performance of Salt Coagulation Method>. With regard to the obtained dried coatings, flexibility, resistance against ethanol water, and moisture permeability were evaluated. The results are shown in Table 8. It should be noted that numerical values of charged raw materials in Table 8 represent contents (% by weight) of respective essential components (A) to (F) in the case where a total amount of the essential components (A) to (F), among the production raw materials, is assumed to be 100%.

TABLE 7

| Charged Raw Material (parts by weight) | No. 19 | No. 28 | No. 29 | No. 30 |
|---|---|---|---|---|
| Polyisocyanate (A) | | | | |
| Millionate MT (a1) | 25.2 | | | |
| Lupranate MI (a1) | | 29.0 | | |
| Millionate NM100 (a1) | | | 29.0 | 28.9 |
| H12MDI (a2) | 26.4 | 15.3 | 15.3 | 15.3 |

TABLE 7-continued

| Charged Raw Material (parts by weight) | No. 19 | No. 28 | No. 29 | No. 30 |
|---|---|---|---|---|
| DC3000 (B) | 12.8 | 180.5 | 180.5 | 180.1 |
| UH300 (C) | 170.6 | 12.8 | 12.8 | 12.8 |
| 1,4-butandiol (D) | 5.2 | 3.1 | 3.1 | 3.1 |
| DMPA (E) | 5.0 | 5.0 | 5.0 | |
| DMBA (E) | | | | 5.5 |
| 30% piperazine hexahydrate (F) | 19.5 | 19.9 | 19.9 | 19.8 |
| Triethylamine | 3.8 | 3.7 | 3.7 | 3.7 |
| NMP | 61.3 | 61.4 | 61.4 | 61.4 |
| MEK | 188.7 | 313.6 | 313.6 | 313.6 |
| Water | 470.9 | 474.7 | 474.7 | 474.8 |

TABLE 8

| Charged Raw Material (wt %) | No. 19 | No. 28 | No. 29 | No. 30 |
|---|---|---|---|---|
| Polyisocyanate (A) | | | | |
| Millionate MT (a1) | 10.2 | | | |
| Lupranate MI (a1) | | 11.7 | | |
| Millionate NM100 (a) | | | 11.7 | 11.6 |
| H12MDI (a2) | 10.6 | 6.2 | 6.2 | 6.2 |
| a1/a2 (molar ratio) | 50/50 | 67/33 | 67/33 | 67/33 |
| DC3000 (B) | 5.2 | 5.2 | 5.2 | 5.2 |
| UH300 (C) | 68.9 | 72.7 | 72.7 | 72.5 |
| 1,4-butandiol (D) | 2.1 | 1.2 | 1.2 | 1.2 |
| DMPA (E) | 2.0 | 2.0 | 2.0 | |
| DMBA (E) | | | | 2.2 |
| Piperazine (F) | 1.0 | 1.1 | 1.1 | 1.1 |
| <Polyurethane aqueous dispersion> | | | | |
| Emulsification state | Good | Good | Good | Good |
| Non-volatile content (wt %) | 25 | 25 | 25 | 25 |
| EO content (wt %) | 2.0 | 2.0 | 2.0 | 2.0 |
| <Film obtained by Salt Coagulation Method> (Flexibility) | | | | |
| 100% modulus (MPa) | 6.3 | 3.9 | 3.3 | 3.2 |
| Evaluation | ○ | ◎ | ◎ | ◎ |
| (Resistance against ethanol water) | | | | |
| Tensile strength (MPa) | 11 | 6.7 | 11 | 10.2 |
| Evaluation | ◎ | ○ | ◎ | ◎ |
| (Moisture permeability) | | | | |
| Degree of moisture permeability (g/m²-24 hrs) | 520 | 550 | 550 | 560 |
| Evaluation | X | ○ | ○ | ○ |
| (Processing performance) | | | | |
| Gelation performance | ◎ | ◎ | ◎ | ◎ |
| Gelation strength | ○ | ○ | ◎ | ◎ |
| Film forming performance | ◎ | ◎ | ◎ | ◎ |

This experiment was performed for studying effects achieved in the case where the EO content in the polyurethane aqueous dispersion was set to the same level as that in the case of No. 19 (2.0%), and an MDI having a greater content of 2,4'-MDI as an isomeric composition was used as the component (a1). From Table 8, No. 28 in which Lupranate MI containing about 50% of 2,4'-MDI was used was evaluated to provide enhanced practical utility in terms of the flexibility, as compared with the case of No. 19 in which Millionate MT containing almost no 2,4'-MDI was used. Further, No. 29 and No. 30 in which Millionate NM100 containing about 90% of 2,4'-MDI was used was evaluated to provide enhanced practical utility in terms of the flexibility, and at the same time, it was evaluated to provide enhanced practical utility in terms of the gelation strength, as compared with the case of No. 19 in which Millionate MT containing almost no 2,4'-MDI was used.

INDUSTRIAL APPLICABILITY

A polyurethane aqueous dispersion of the present invention has practical utility in terms of the processing suitability when a formed film is produced from the same by salt coagulation method, and an obtained formed film has practical utility in terms of the resistance against ethanol water. Therefore, the present invention is applicable for the production of a formed film by salt coagulation method, and is applicable as a formed film.

The invention claimed is:

1. A polyurethane aqueous dispersion for a formed film, the formed film being obtained by using the polyurethane aqueous dispersion and a coagulant liquid in combination, wherein the polyurethane aqueous dispersion being obtained by:
   neutralizing an isocyanate group-terminated prepolymer obtained by reaction of:
      a polyisocyanate (A) composed of diphenylmethane diisocyanate (a1) and alicyclic diisocyanate (a2);
      a random copolymer (B) of ethylene oxide and tetrahydrofuran;
      a polyol (C) having a number average molecular weight of 1000 to 5000;
      a polyhydric alcohol-based chain extender (D) having a number average molecular weight of 400 or less; and
      a diol compound (E) having a carboxyl group, and
   dispersing the obtained neutralized substance in water,
   and thereafter causing a chain extension reaction using an amine-based chain extender (F).

2. The polyurethane aqueous dispersion according to claim 1, wherein a molar ratio between the component (a1) and the component (a2), which is (a1)/(a2), is in a range of 20/80 to 80/20.

3. The polyurethane aqueous dispersion according to claim 2, wherein the component (a2) is at least one selected from the group consisting of hydrogenated diphenylmethane diisocyanate and isophorone diisocyanate.

4. The polyurethane aqueous dispersion according to claim 1, wherein the component (B) has a number average molecular weight of 800 to 4000, and a molar ratio between units of the ethylene oxide (EO) and units of tetrahydrofuran (THF), which is EO/THF, is in a range of 80/20 to 10/90.

5. The polyurethane aqueous dispersion according to claim 4, wherein a content of EO is 2.8% by weight or more with respect to polyurethane in the polyurethane aqueous dispersion.

6. The polyurethane aqueous dispersion according to claim 5, wherein the content of EO is 2.8% by weight to 14% by weight.

7. The polyurethane aqueous dispersion according to claim 4, wherein a content of 2,4'-diphenylmethane diisocyanate (2,4'-MDI) in the component (a1) is 40% by weight or more.

8. The polyurethane aqueous dispersion according to claim 7, wherein the content of 2,4'-MDI is 70% by weight or more.

9. A formed film obtained by using the polyurethane aqueous dispersion according to claim 1 and a coagulant liquid in combination.

10. A glove obtained by using the polyurethane aqueous dispersion according to claim 1 and a coagulant liquid in combination.

* * * * *